United States Patent [19]

Smith et al.

[11] 4,076,942

[45] Feb. 28, 1978

[54] CRYSTALLINE DIPILOCARPINIUM PAMOATE

[75] Inventors: Robert L. Smith, Lansdale; Ta-Jyh Lee, Hatfield, both of Pa.

[73] Assignee: Merck & Co., Inc., Rahway, N.J.

[21] Appl. No.: 618,538

[22] Filed: Oct. 1, 1975

[51] Int. Cl.² ............................................ C07D 405/06
[52] U.S. Cl. ................................. 548/336; 424/273 R
[58] Field of Search ........................................ 260/309

[56] References Cited

FOREIGN PATENT DOCUMENTS 2,459,391  6/1975  Germany ............................. 260/309

OTHER PUBLICATIONS

Weissberger, Ed. Technique of Organic Chemistry, vol. III, Part I, Separation and Purification, pp. 817–835, N. Y., Interscience Pub., 1956.

Morton Laboratory Technique in Organic Chemistry, 1st Ed., pp. 148, 161 and 232–236, N. Y., McGraw-Hill, 1938.

Primary Examiner—Natalie Trousof
Attorney, Agent, or Firm—Edmunde D. Riedl; Raymond M. Speer; Mario A. Monaco

[57] ABSTRACT

This invention relates to novel crystalline dipilocarpinium pamoate useful as an agent, for lowering elevated intraocular pressure in glaucomatous patients, as well as to a process for preparing said compound and novel intermediates thereof.

4 Claims, No Drawings

CRYSTALLINE DIPILOCARPINIUM PAMOATE

BACKGROUND OF THE INVENTION

Pilocarpine, its polyuronic acid salts, nitrate, as well as other salts, are known to be useful in the treatment of glaucoma, a symptomatic condition often characterized by elevated intraocular pressure. U.S. Application Ser. No. 553,399 filed Feb. 26, 1975, now abandoned, discloses and claims amorphous dipilocarpinium pamoate. Although this amorphous salt is useful in glaucoma therapy (e.g., extends duration of ocular hypotensive activity relative to that observed with previously described pilocarpine salts), its amorphous nature presents a drawback in not being readily and easily handleable, in being difficult to formulate in an appropriate ocular delivery system and in being difficult to generate stoichiometrically. We have found that crystalline dipilocarpinium pamoate readily overcomes the present difficulties encountered with the amorphous material.

The amorphous dipilocarpinium pamoate as disclosed in said application is prepared by a technique well known in the art for preparing salts. For example, pilocarpine and pamoic acid are suspended in an aqueous medium and the salt thus prepared is isolated by removal of water. This technique, however, leads to an oily material which must be placed in an oven to obtain solid dipilocarpinium pamoate. The salt thus obtained, however, is amorphous and not crystalline; in addition, one cannot be certain that the ratio of pilocarpine to pamoic acid will be 2:1.

We have found a novel process for preparing crystalline dipilocarpinium pamoate employing unique conditions which lead to substantially pure dipilocarpinium pamoate having a ratio of 2:1 of pilocarpine to pamoic acid.

DETAILS OF THE INVENTION

General methods for the preparation of dipilocarpinium pamoate (as would be used in the preparation of a salt from its corresponding acid and base) results in a solvate of said compound. The solvate arises from the solvent, for example, water that was used as the salt preparation medium. Desolvating the solvated compound generally results in an amorphous salt. For example, if instead of water, isopropanol or chloroform is the moiety forming the solvate with the salt, desolvating results in an amorphous material as well. Furthermore, other solvents such as dimethylformamide (DMF), dimethylsulfoxide (DMSO), or hexamethyl phosphoric triamide (HMPA) which could be employed as a solvent in the preparation of the salt, form a solvate of the salt which is quite difficult to separate.

We have found that a lower alkyl ketone solvate of the dipilocarpinium salt can be not only readily removed but surprisingly leads to a novel crystalline material. The ketone that forms the solvate may be described by the following structural formula:

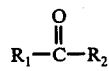

(I)

wherein $R_1$ and $R_2$ are independently selected from alkyl radicals of from 1-3 carbon atoms. Thus, the ketone may be acetone, methylethyl ketone and the like, especially acetone. As a further aspect of this invention, the ketone solvates are novel compounds. In accordance with one aspect of this invention, the dipilocarpinium pamoate ketone solvate is subjected to vacuum with or without heat until the ketone is substantially removed. The resulting product obtained is substantially free of the ketone and in a crystalline form. The uniqueness of this invention resides in the fact that only the ketone solvate is capable of undergoing desolvation leading to crystalline dipilocarpinium pamoate. This is indeed surprising since, as previously indicated, the use of other solvents in attempting to prepare the crystalline material either leads to amorphous dipilocarpinium pamoate upon desolvation or cannot be removed but rather remain as solvates.

More specifically, the crystalline dipilocarpinium pamoate ketone solvate is subjected to a partial vacuum of 100 to 0.005 mm. Hg at 20° to 60° C; preferably, 0.15 to 0.005 mm. Hg of vacuum at 55° to 60° C is used to remove the ketone.

The ketone solvate may be prepared in a number of ways. For example, a solution of pilocarpine and pamoic acid is prepared by stirring pilocarpine and pamoic acid in a polar solvent such as DMSO, HMPA, DMF or ketone I, or a mixture of ketone I and water. Although this reaction can be carried out by stirring a stoichiometric (2:1) ratio of pilocarpine to pamoic acid, it is preferred that at least a 10% excess of pilocarpine and preferably a 40–100% excess be used in order to be certain to obtain substantial dipilocarpinium pamoate rather than some monopilocarpinium pamoate as well. The dipilocarpinium pamoate salt thus obtained is isolated in the form of the solvate (depending upon the solvent used) by either adding a non-polar solvent to the point of incipient turbidity or by removing some of the polar solvent to the point of incipient turbidity and then cooling to facilitate the precipitation of the dipilocarpinium pamoate solvate. Any non-reactive non-polar solvent such as chloroform, acetone, diethyl ether, or hexane may be used to initiate the precipitation of the salt. The precipitated solvated dipilocarpinium pamoate is then separated by filtration. The solvated salt is then redissolved in a ketone (previously described (I)) and the solvent subsequently evaporated with or without vacuum to obtain a solid. This procedure of dissolving and reprecipitation is repeated until the residue is free of the polar solvent. The final residue is redissolved in the ketone at which point either some ketone solvent is removed or a sufficient amount of a non-polar solvent such as hexane, benzene or diethyl ether is added to incipient turbidity. The mixture is then cooled for a sufficient period until substantially all of the ketone solvate of the dipilocarpinium pamoate is precipitated. As an alternative, one could dissolve the pilocarpine and pamoic acid in a ketone alone (Compound I) or in a mixed solvent system (such as ketone I and water) to form the salt. In this alternate procedure the ketone solvate is formed directly. This solvate has a molar ratio of 1 ketone to 1 dipilocarpinium pamoate. This solvate is a novel compound and another aspect of this invention. The precipitate is then collected and the ketone removed by drying as described previously. The resulting optically pure, stoichiometric dipilocarpinium pamoate is obtained in a crystalline form having a melting point of ≧111° C and a characteristic X-ray defraction pattern with peaks corresponding to two theta from 7.4° to 25.9°, with specific major peaks at 7.4°, 9.0°, 11.9° and 19.7°. The salt should contain ≦5% of amorphous material, and preferably, it should be substantially free of any amorphous material (less than 1%).

Furthermore, the desolation should be substantially complete (less than 0.1% as solvate). The crystalline dipilocarpinium pamoate is further characterized in having a melting point of $\geq 111°$ C. This melting point represents about 5% amorphous dipilocarpinium pamoate content.

The following crystalline and amorphous dipilocarpinium pamoate mixtures were made up and their melting points were measured in capillary tubes in a pre-calibrated oil bath. (Thomas Hoover capillary melting point apparatus). The composition of the mixture:

| % Crystalline salt + | % Amorphous salt | m.p.* (corrected) °C |
|---|---|---|
| 100 | 0 | 114 |
| 95 | 5 | 111 |
| 90 | 10 | 108 |
| 75 | 25 | 104 |
| 50 | 50 | 91 |
| 0 | 100 | 73 |

*m.p. here defined as the temperature sample begins to shrink.

Pilocarpine, the active ingredient of the subject compound, is a well-known therapeutic agent for lowering elevated intraocular pressure and causing miosis in glaucomatous eyes of higher primates including man. However, in experimental animals such as the rabbit, pilocarpine elicits only miosis. Since the duration of intraocular hypotensive activity elicited by pilocarpine in human patients with glaucoma is usually twice the duration of miosis in rabbits, evaluation of miotic activity in rabbits serves as a biological assay for the desired antiglaucoma activity. An extended duration of miosis was observed in rabbits treated with the subject compound. The following test procedure was employed:

Randomized series of six male and female New Zealand albino rabbits weighing 3–3.5 kg., approximately 4–5 months of age, were used. The animals were kept in restraint boxes in a room with a steady light of weak intensity. The naive animals were accustomed to the experimental conditions (laboratory, restraint boxes...) once before time of testing. The same rabbits were re-used with at least 14 days rest between two testings; they were finally eliminated after five times. The animals were accustomed to the environment for 1 hour, and after initial measurements, the compounds to be studied were administered (solutions, rods, discs, ointment...) into the conjunctival sac of the eye and the other non-treated eye was the control. The pupil measurements were made 5, 30, 90, 210 and 360 minutes after treatment. The average pupil diameters and confidence limits for P $\leq 0.05$ of each series (six rabbits) were given. The pupil diameter was measured with a LUNEAU and COFFIGNON pupillometer whose principle of operation consists in superimposing the virtual image of a red light beam of variable diameter into the plane of the iris. With an adjustable diaphragm, one adjusts the diameter of the bundle of red light rays to coincide with that of the pupil. The diameter of the diaphragm is recorded directly in millimeters. The results of these tests are shown in the following table:

REPRESENTATIVE TEST DATA FOR VARIOUS DIPILOCARPINIUM PAMOATE PREPARATIONS
(INITIALLY CRYSTALLINE)

| I. Insert Formulation | Klucel Type | Duration of Miosis Measurement (hr.) | Area Under Miosis Curve (cm²) |
|---|---|---|---|
| A. Compression molded, rectangular shape (12.5 mm. × 1.8 mm. × 0.6 mm.), 33.3% pamoate salt - 66.7% klucel; each insert contains ~ 2 mg. pilocarpine free base | HF | 7 | 32 (10) |
|  | GF | 7 | 32 (10) |
| B. Injection molded, rod shape (1.25 mm. diam. × 10.0 mm. long), 33.3% pamoate salt - 66.7% klucel; each insert contains ~ 2 mg. pilocarpine free base | HF | 11 | 38 (10) |
|  | HF | 11 | 40 (10) |
| C. Extrusion molded, rod shape (1.25 mm. diam. × 10 mm. long), 33.3% pamoate salt - 66.7% klucel; each insert contains ~ 2 mg. pilocarpine free base | HF | 11 | 40 (10) |
| D. Compression molded, lenticular shape: | | | |
| Pilocarpine free base content (in mg.)/14 mg. total insert weight | | | |
| 2.0  GF | | 6 | 29 (6) |
| 0.5  GF | | 6 | 24 (6) |
| 2.1  HG | | 6 | 31 (6) |

| II. Ointment Formulation | Duration of Miosis Measurement (hr.) | Area Under Miosis Curve (cm²) |
|---|---|---|
| 10 mm. ribbon of crystalline pamoate salt in petrolatum vehicle (= to ~ 1 mg. of pilocarpine free base) - note: 16.4% crystalline pamoate salt, 83.6% petrolatum by weight | 6 | 16 (6) |
| but using amorphous pamoate salt | 6 | 11 (6) |

-continued

REPRESENTATIVE TEST DATA FOR VARIOUS DIPILOCARPINIUM PAMOATE PREPARATIONS
(INITIALLY CRYSTALLINE)

III. Solution Formulation
3.864 mg. of pamoate salt was dissolved in ~ 50 μl. of a solvent composed of 10% polyvinylpyrrolidone in water (4.9 ml.) + tween 80 (0.1 ml.)- affording a clear solution for a single topical instillation; dose = 2.0 mg.     4 (crystalline)     18 (6)

pilocarpine free base     4 (amorphous)     21 (6)

Legend:
1. Only in the Ointment Formulations are the dipilocarpinium pamoate salts applied in their initial physical states (crystalline vs. amorphous)
2. Area Under Miosis Curve numbers:
Area under curve shown outside of parentheses; number of rabbits used to determine the $cm^2$ numbers shown inside of parentheses.

An extended duration of miosis was observed in these animals after administration of medications prepared as herein described including between about 1 and 10% active ingredient.

The product prepared by the process of this invention is administered topically to the eye, in the form of ophthalmic solutions, as ophthalmic ointments, in solid form or mixed with a solid insert. Formulations are herein expressed as percent weight by volume and generally the dosages necessary for lowering elevated intraocular pressure fall within the range of 1 to 7%. Higher dosages, as for example, up to about 10%, or lower dosages can be employed, provided the dose is effective in lowering intraocular pressure and is non-irritating.

The product of this invention is incorporated into a sterile ophthalmic vehicle. Such vehicles are well known in the art and are fully described in such standard reference works as Remington's Pharmaceutical Sciences, Martin and Cook, Mack Publishing Co., Easton, 13th editon (1965).

The following examples are given by way of illustration.

EXAMPLE 1

Preparation of Crystalline Dipilocarpinium Pamoate

Step A — Preparation of Crystalline Dipilocarpinium Pamoate Acetone Solvate

Pamoic acid (388 mg., 1.0 millimole) is added to a freshly prepared solution of pilocarpine (416 mg., 2.0 millimole) in dry DMF (0.4 ml.) at 20°. The resulting suspension is stirred at 20° for 25 minutes, affording a clear solution which is diluted slowly with acetone (4 ml.) to incipient turbidity and stored at 5°–10° for 72 hours. Deposited solid is collected by filtration and found to be solvated with both acetone (pmr singlet at δ2.05) and DMF (pmr singlets at δ2.65, 2.8 and 7.93). The solid is suspended in acetone (25 ml.) at 20° for 5 minutes providing a fine suspension which is evaporated in vacuo at 70° leaving a residual solid. This process, acetone suspension-in vacuo solvent removal, is repeated three times leaving a crystalline residue which is collected and dried at 20° for 1 hour affording the title compound as pale yellow crystals (723 mg., 85%), m.p. 84° C with dec.; $[\alpha]_D^{24}+51.6°$ (C=1.4, $CH_3OH$); pmr ($d_6$-DMSO) δ2.05 (6H, s) and peaks recorded for title compound in Step B below; crystallinity is established by X-ray powder diffraction analysis.

When dimethylsulfoxide is used in place of DMF in part A above, similar results are obtained.

Step B — Preparation of Crystalline Dipilocarpinium Pamoate

Crystalline dipilocarpinium pamoate.acetone solvate (723 mg., 0.85 millimole) is placed in a drying pistol maintained at 55°–60° and under a partial vacuum of 0.15–0.005 mm. Hg. for 22 hours providing the title compound as pale yellow crystals (684 mg., 100%), m.p. 114°–116° C with dec.; $[\alpha]_D^{24}+55.6°$ (C=1.0, $CH_3OH$); pmr ($d_6$-DMSO) δ1.13 (6H, t), 1.73 (4H, broad quintet), 2.4–3.3 (8H + DMSO, m), 3.8 (6H, s), 3.95–4.55 (4H, m), 4.9 (2H, s), 7.1–7.5 (6H, m), 7.9 (2H, d), 8.3 (2H, d), 8.4 (2H, s), 8.8 (2H, s) and 11.5 (4H, broad s); crystallinity is established by X-ray powder diffraction analysis; GC analysis indicates greater than 95% optical purity (pilocarpine content).

EXAMPLE 2

Preparation of Crystalline Dipilocarpinium Pamoate

Step A — Preparation of Crystalline Dipilocarpinium Pamoate 2-Butanone Solvate

This compound is prepared essentially by the same procedure described in Example 1, Step A, employing the following reagents:

Pamoic acid: 388 mg., 1.0 millimole
Pilocarpine: 416 mg., 2.0 millimole
DMF: 0.4 ml.
2-Butanone: 104.0 ml.

The title compound is obtained as pale yellow crystals (702 mg., 80%), m.p. 114° C with slow dec.; $[\alpha]_D^{24}+58.9°$ (C=0.4, $CH_3OH$); pmr ($d_6$-DMSO) δ0.9 (3H, t), 2.05 (3H, s), 2.3 (2H, quartet) and peaks recorded for the title compound in Example 1, Step B; crystallinity is established by X-ray powder diffraction analysis.

Step B — Preparation of Crystalline Dipilocarpinium Pamoate

This compound is prepared essentially by the same procedure described in Example 1, Step B, employing the following reagent:

Crystalline dipilocarpinium.pamoate.2-butanone solvate (702 mg., 0.8 millimole).

The title compound is obtained as pale yellow crystals (644 mg., 100%) and is identical to an authentic sample as prepared in Example 1, Step B, via m.p., $[\alpha]_D^{24}$, pmr. X-ray powder diffraction analysis and optical purity.

EXAMPLE 3

Preparation of Crystalline Dipilocarpinium Pamoate

Step A — Preparation of Crystalline Dipilocarpinium Pamoate. Acetone Solvate

Pamoic acid (388 mg., 1.0 millimole) is added to a freshly prepared solution of pilocarpine (416 mg., 2.0 millimole) in dry DMF (0.4 ml.) at 20°. The resulting suspension is stirred at 20° for 25 minutes affording a clear solution which is evaporated in vacuo at 70° using a rotoray evaporator. The residual solid is suspended in acetone (25 ml.) at 20° for 5 minutes providing a fine suspension which is evaporated in vacuo at 70° leaving a residual solid. This process, acetone suspension-in vacuo solvent removal, is repeated three times to ultimately provide the title compound as pale yellow crystals (706 mg., 83%) identical to an authentic sample as prepared in Example 1, Step A, via m.p., $[\alpha]_D^{24}$, pmr and X-ray powder diffraction analysis.

Step B — Preparation of Crystalline Dipilocarpinium Pamoate

Crystalline dipilocarpinium pamoate acetone solvate (723 mg. 0.85 millimole) is placed in a drying pistol maintained at 55°-60° and under a partial vacuum of 0.15-0.005 mm. Hg. for 22 hours providing the title compound as pale yellow crystals (684 mg., 100%), m.p. 114°-116° C with dec.; $[_D^{24}+55.6°$ (C=1.0, CH$_3$OH); pmr (d$_6$-DMSO) δ1.13 (6H, t), 1.73 (4H, broad quintet), 2.4–3.3 (8H + DMSO, m), 3.8 (6H, s), 3.95–4.55 (4H, m), 4.9 (2H, s), 7.1-7.5 (6H, m), 7.9 (2H, d), 8.3 (2H, d), 8.4 (2H, s), 8.8 (2H, s) and 11.5 (4H, broad s); crystallinity is established by X-ray powder diffraction analysis; GC analysis indicates greater than 95% optical purity (pilocarpine content).

EXAMPLE 4

Crystalline Dipilocarpinium Pamoate

Pilocarpine, 388 g. (1.86 moles) is dissolved in 9599 ml. of acetone and warmed at 55°. The pamoic acid 247 g. (0.693 mole), is added and the mixture held at 50°-55° for 30 minutes. The slightly turbid solution is filtered while hot through acetone-washed Super-Cel followed by 1773 ml. of hot acetone.

The filtrate is then seeded with crystals of the 2:1 salt-acetone solvate and cooled in an ice bath for 30 minutes with stirring.

Hexane, 2206 ml., is added and the mixture filtered and washed with 1791 ml. of ether in three portions.

The filter cake is dried in vacuo at 55°-60° to give the subject compound, weight = 506.19 g., 90.7% based on pure pamoic acid.

EXAMPLE 5

Insert Dosage Form

Dipilocarpinium Pamoate Equivalent to 2 mg. of Pilocarpine Base. Hydroxypropylcellulose q.s. ad, 12 mg.

Compression Molding — Ophthalmic inserts are manufactured from compression molded films which are prepared on a Carver Press by subjecting the powder mixture to a compressional force of 12,00 lbs. (gauge) at 300° F for 1 to 4 minutes. The film is cooled under pressure by having cold water circulate in the platen. Ophthalmic inserts are then individually cut from the film with an oval shaped punch. Each insert is placed into a vial, which is then placed in a humidity cabinet (88% R.H. at 30° C) for 2 to 4 days. After removal from the humidity cabinet, the vials are stoppered and then capped. The vials containing the hydrated insert are then autoclaved at 250° F for a ½ hour.

EXAMPLE 6

Suspension Dosage Form of Dipilocarpinium Pamoate

| | |
|---|---|
| Dipilocarpinium pamoate | 4 mg. |
| Cellosize QP 100 ML | 1.5 mg. |
| Benzalkonium chloride | 0.2 mg. |
| Tween 80 | 1.0 mg. |
| Benzylalcohol | 1.0 mg. |
| Phenylethanol | 1.0 mg. |
| Sodium chloride q.s. | isotonicity |
| Water for Injection q.s. ad. | 1.0 ml. |

Directions for Manufacture

Dissolve cellosize QP 100 ML in part of the Water for Injection. Then pass the solution through a coarse filter and autoclave to achieve sterility. Place pilocarpine salt and sodium chloride in a quantity of water sufficient to dissolve the sodium chloride. Then autoclave to achieve sterility. To the third portion of Water for Injection, add benzalkonium chloride, Tween 80, benzylalcohol, phenylethanol. Pass this solution through a sterilization pad (0.22 micron). Aseptically combine the two sterile solutions with the sterile suspension.

What is claimed is:

1. Substantially crystalline, optically pure dipilocarpinium pamoate.

2. Substantially crystalline, optically pure dipilocarpinium pamoate of claim 1 having a melting point greater than 111° C and X-ray diffraction pattern peaks corresponding to two theta from 7.4° to 25.9°, with specific major peaks at 7.4°, 9.0°, 11.9° and 19.7°.

3. A dipilocarpinium pamoate ketone solvate wherein the ketone moiety is:

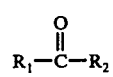

wherein R$_1$ and R$_2$ are independently selected from alkyl groups of from 1 to 3 carbon atoms, having a molar ratio of ketone to dipilocarpinium pamoate of about 1:1.

4. Dipilocarpinium pamoate acetone solvate.

* * * * *